United States Patent [19]

Martin

[11] 4,246,423
[45] Jan. 20, 1981

[54] SILICONE POLYETHER COPOLYMERS
[75] Inventor: Eugene R. Martin, Onsted, Mich.
[73] Assignee: SWS Silicones Corporation, Adrian, Mich.
[21] Appl. No.: 86,906
[22] Filed: Oct. 22, 1979
[51] Int. Cl.³ .............................................. C07F 7/10
[52] U.S. Cl. .................................... 556/423; 427/387; 427/394; 427/396; 427/412; 428/224; 106/287.11; 260/404; 260/404.5; 427/372.2; 427/430.1; 427/443.1
[58] Field of Search .............. 556/423; 260/404, 404.5
[56] References Cited
U.S. PATENT DOCUMENTS

| 3,694,480 | 9/1972 | Omiotanski | 556/423 X |
| 4,088,670 | 5/1978 | Bargain et al. | 556/423 X |

Primary Examiner—Paul F. Shaver

[57] ABSTRACT

Silicone polyether copolymers having the general formula

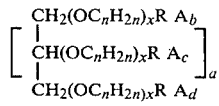

wherein R is a radical selected from the group consisting of

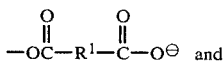 and

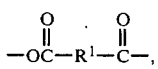

in which the radical R is linked to the polyether through an ester linkage, $R^1$ is a divalent hydrocarbon radical selected from the group consisting of $(-CH_2)_y$, $-CH=CH-$, or a cyclic radical selected from the group consisting of $C_6H_4$, $C_6H_8$ and $C_{10}H_6$; A is a silicone containing monovalent or divalent radical selected from the group consisting of

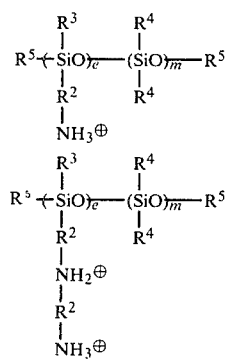

-continued

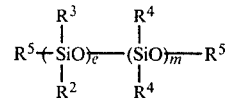

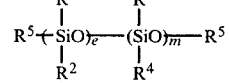

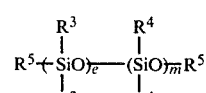

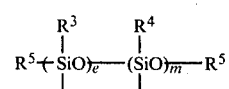

$R^2$ is selected from the group consisting of saturated divalent hydrocarbon radicals, hydrocarbonoxy radicals in which the hydrocarbon group is linked to the silicon by a carbon bond and the oxygen is in the form of an ether linkage, and unsaturated divalent hydrocarbon radicals, $R^3$ is selected from the group consisting of monovalent hydrocarbon radicals having from 1 to 18 carbon atoms, alkoxy radicals having from 1 to 18 carbon atoms and $OSi(R^4)_3$ radicals, $R^4$ is a monovalent hydrocarbon radical having from 1 to 18 carbon atoms, $R^5$ is a monovalent radical selected from the group consisting of $O_{0.5}SI(R^4)_3$ and $O_{0.5}R^4$, where $R^4$ is the same as above, and when R is cationic, then A must be anionic and when R is nonionic then A must be nonionic, a is a number of from 0 to 4, b, c and d are each numbers of from 0 to 1, the sum of b, c and d must be at least 1 when A is a monovalent radical and when A is a divalent radical the sum of b, c and d must be at least 0.5 and up to 3 with the proviso that when c is greater than 0 then a must be at least 1, e is a number of from 1 to 200, m is a number of from 1 to 20,000, n is 2, 3 or 4, x is a number of from 1 and up to 400, preferably from 10 to 250 and y is a number of from 0 to 8. These silicone polyether copolymers may be used alone or in combination with other textile treating agents to impart oleophobic and hydrophobic properties thereto.

17 Claims, No Drawings

SILICONE POLYETHER COPOLYMERS

The present invention relates to silicone polyether copolymers, particularly to a process for preparing silicone polyether copolymers and more particularly to a process for treating textile materials with silicone polyether copolymers to impart oleophobic and hydrophobic properties thereto.

BACKGROUND OF INVENTION

Silicone polyether copolymers are well known in the art and their use as lubricants for organic fibers is described in U.S. Pat. No. 2,868,824 to Haluska. The silicone polyether copolymers described in U.S. Pat. No. 2,868,824 may be prepared by interacting the dialkenyl ethers of glycols or polyglycols with a copolymeric siloxane in which some of the silicon atoms contain silicon bonded hydrogen atoms in the presence of a platinum catalyst.

Also, U.S. Pat. No. 2,846,458 to Haluska discloses organosiloxane ethers which contain a hydrophilic and a hydrophobic portion in the molecule. These organosiloxane ethers may also be prepared by reacting an unsaturated ether with an organosiloxane containing an SiH group in the presence of platinum catalysts.

The organosiloxane ether copolymers described above have certain disadvantages. For example, these compositions contain residual amounts of silicon-bonded hydrogen atoms which slowly release hydrogen during storage. Moreover, in certain applications, it is often desirable to combine basic or protic solvents with these organosiloxane ethers; however, these protic solvents or basic materials often react with the organosiloxane ethers containing residual Si-H groups to cause foaming, pressure build-up in containers and in certain instances gellation of the copolymers. Furthermore, polyethers having terminal unsaturation which are required to form the organosiloxane-polyether copolymers are not commercially available.

U.S. Pat. No. 3,057,901 to Plueddemann describes hydroxyether organosilicon compounds which are prepared by reacting allyl glycidyl ether or butadiene monoepoxide with polymeric siloxanes containing Si-H groups in the presence of platinum catalysts. The resultant product is then reacted with an alcohol, such as glycols, to form the hydroxyether organosilicon compounds. These compositions also have certain disadvantages since they contain residual amounts of silicon-bonded hydrogen.

In contrast to the compositions described in the above patents, the polyether units are linked to a silicon atom through an amido or ammonium ion. The resultant silicone polyether copolymers are water soluble and are capable of being crosslinked to form continuous films. Furthermore, the process of this invention provides a unique method for converting low viscosity fluids to high viscosity materials.

Therefore, it is an object of this invention to provide novel silicone polyether copolymers. Another object of this invention is to provide silicone polyether copolymers which are essentially free of silicon bonded hydrogen. A further object of this invention is to provide a process for preparing novel silicone polyether copolymers. A still further object of this invention is to provide a process for preparing novel silicone polyether copolymers from materials which are readily available.

SUMMARY OF INVENTION

The foregoing objects and others which will become apparent from the following description are accomplished, in accordance with this invention, generally speaking, by providing silicone polyether copolymers having the general formula

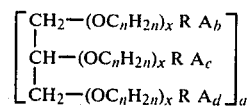

wherein R is a radical selected from the group of

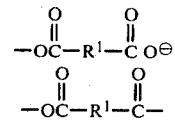

where the radical R is linked to the polyether by an ester linking and is linked to A by an amide or an ammonium salt linkage, $R^1$ is a divalent radical selected from the group consisting of $-(CH_2)_y$, $-CH=CH-$, or a cyclic radical selected from the group consisting of $C_6H_4$, $C_6H_8$ and $C_{10}H_6$; A is a silicone containing monovalent or divalent radical selected from the group

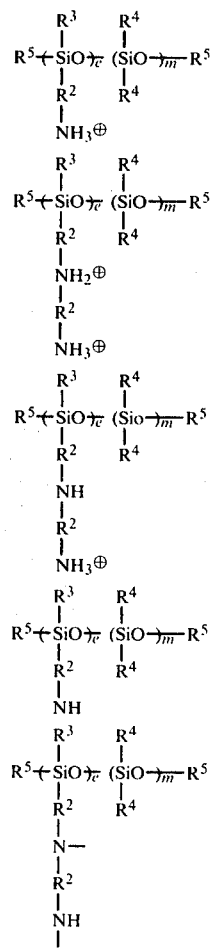

-continued

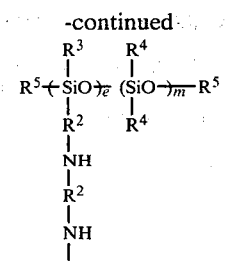

$R^2$ is selected from the group consisting of saturated divalent hydrocarbon radicals, hydrocarbonoxy radicals in which the hydrocarbon group is linked to the silicon by a carbon bond and the oxygen is in the form of an ether linkage and unsaturated divalent hydrocarbon radicals, $R^3$ is selected from the group consisting of monovalent hydrocarbon radicals having from 1 to 18 carbon atoms, alkoxy radicals having from 1 to 18 carbon radicals, or an $OSi(R^4)_3$ radical, $R^4$ is a monovalent hydrocarbon radical having from 1 to 18 carbon atoms, $R^5$ is a monovalent radical selected from the group consisting of $O_{0.5}Si(R^4)_3$ and $O_{0.5}R^4$ in which $R^4$ is the same as above, a is a number of from 0 to 4, b, c and d are 0 or 1, the sum of b, c and d must be at least 1 when A is a monovalent radical, and when A is a divalent radical, the sum of b, c and d must be at least 0.5, and up to 3 with the proviso that when e is greater than 0 then A must be at least 1, e is a number of from 1 to 200, m is a number of from 1 to 20,000, n is 2, 3 or 4, x is a number of from 1 to 400, and y is a number of from 0 to 8.

When R is cationic then A must be anionic and when R is nonionic then A must be nonionic. The unsatisfied valences of A are satisfied by R and when A is a divalent radical then the ratio of A to R is 1 to 2.

DETAILED DESCRIPTION OF INVENTION

In the silicone polyether copolymers of this invention, $R^1$ is a divalent radical which is derived from the reaction of a cyclic anhydride or a dicarboxylic acid with an oxyalkylene glycol or copolymers thereof.

Examples of divalent radicals represented by $R^1$ above having from 1 to 10 carbon atoms are alkylene radicals such as methylene, ethylene, trimethylene tetramethylene, pentamethylene, hexamethylene, octamethylene and decamethylene radicals. Examples of divalent cyclic radicals represented by $R^1$ are phenylene, naphthenylene and cyclohexenylene radicals.

Examples of suitable divalent hydrocarbon radicals represented by $R^2$ are alkylene radicals such as ethylene, trimethylene, hexamethylene and octamethylene radicals. Examples of hydrocarbonoxy containing radicals are radicals of the formula $(C_2H_4O)_r(CH_2)_z$, $(C_3H_6O)_r(CH_2)_z$ and $(C_4H_8O)_r(CH_2)_z$ where r is from 1 to 50, and z is a number of from 1 to 10, ethylene oxide, trimethylene oxide, tetramethylene oxide and polymers and copolymers thereof and alkenylene radicals such as vinylene, propenylene, butenylene, hexenylene and the like.

Suitable examples of monovalent hydrocarbon radicals represented by $R^3$ and $R^4$ are alkyl radicals, e.g., methyl, ethyl, propyl, butyl, hexyl, octyl, decyl, dodecyl and octadecyl radicals; aryl radicals, e.g., the phenyl radical; alkaryl radicals, e.g., tolyl, xylyl and ethylphenyl radicals; cycloalkyl radicals, e.g., cyclobutyl, cyclohexyl, cyclodecyl radicals; aralkyl radicals, e.g., benzyl, 2-phenylethyl and 2-phenylpropyl radicals.

Examples of alkoxy radicals represented by $R^3$ having from 1 to 18 carbon atoms are methoxy, ethoxy, propoxy, butoxy, octoxy, dodecoxy and octadecoxy radicals.

The silicone polyether copolymers of this invention may be prepared by several different methods. Some of the methods for preparing these silicon polyether copolymers are described below.

A preferred method for preparing the silicone polyether copolymers is to react oxyalkylene glycols or copolymers thereof with a mono cyclic acid anhydride at a temperature of from 80° to 185° C. to form a half ester which is then reacted with aminofunctional silicone fluids having the formulas

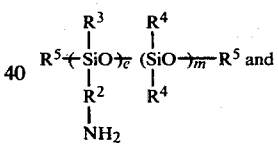

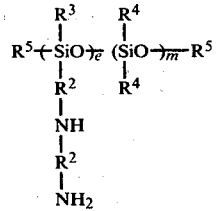

where $R^2$, $R^3$, $R^4$, $R^5$, e and m are the same as above, at a temperature of from 25° to 110° C.

The reaction described above may be further illustrated by the following equations:

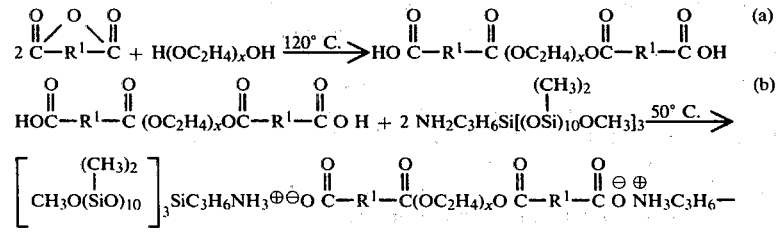

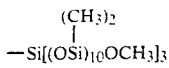

where $R^1$ and x are the same as above.

Another method for preparing the silicone polyether copolymers is to react oxyalkylene glycols or copolymers thereof with a monocyclic anhydride at a temperature of from 80° to 185° C. to form a half ester and then react the resultant product with the aminofunctional silicone fluids described above at a temperature of from 115° to 175° C. to form silicone polyether copolymers in which the silicone is linked to the polyether by an ester-amide linkage. The reaction may be further illustrated by the following equations:

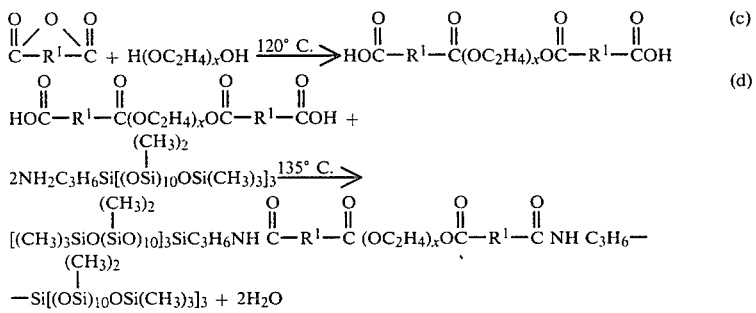

The silicone polyether copolymers of this invention may also be prepared by substituting dicarboxylic acids having up to 10 carbon atoms for the cyclic acid anhydrides described above.

When dicarboxylic acids are used, it may be advantageous to employ an esterification catalyst such as titanates, alkali metal hydroxides and mineral acids in the reaction.

Suitable examples of dicarboxylic acids which may be used are oxalic acid, malonic acid, succinic acid, glutaric acid, adipic acid, pimelic acid, suberic acid, azelaic acid and sebacic acid.

The oxyalkylene glycols and copolymers thereof which may be used to prepare the compositions of this invention are well known in the art. These glycol polymers and copolymers may be illustrated by the following formula:

$$\begin{bmatrix} CH_2-(OC_nH_{2n})_xOG \\ CH-(OC_nH_{2n})_xOG \\ CH_2-(OC_nH_{2n})_xOG \end{bmatrix}_a,$$

where G is hydrogen or an alkyl radical having from 1 to 18 carbon atoms, in which at least one G must be hydrogen, a is a number of from 0 to 4, n is 2, 3 or 4, and x is a number of at least 1 and up to 600, preferably from 10 to 250. Generally, these glycol polymers are prepared from the homopolymerization or copolymerization of ethylene oxide and propylene oxide using various alcohols as initiators. Examples of suitable alcohols are glycerine, methanol, ethylene glycol, ethanol, t-butanol and the like.

In the above formula, the examples cited for the $R^4$ radical are equally applicable for the G radicals.

Suitable examples of cyclic anhydrides which may be used to prepare the compositions of this invention are succinic anhydride, glutaconic anhydride, maleic anhydride, 1,2-cyclohexanedicarboxylic anhydride, 1-cyclohexene-1,2-dicarboxylic anhydride, 3-cyclohexene-1-2-dicarboxylic anhydride, 4-cyclohexene-1, 2 dicarboxylic anhydride, 1, 8 -napthalic acid anhydride and phthalic anhydride.

The aminofunctional silicone fluids employed in the process of this invention are well known in the art. They may be prepared in accordance with the process described in U.S. Pat. No. 2,947,771 to Bailey, in which an aminofunctional silane is equilibrated with a siloxane in the presence of an alkali-metal hydroxide. Also, they may be prepared in accordance with the process described in U.S. Pat. No. 3,598,853, to Friedman et al, in which an aminofunctional silane is condensed with a silanol terminated polydiorganosiloxane. Other methods for preparing aminofunctional silicone fluids are described in U.S. Pat. Nos. 3,890,269 to Martin, 2,930,809 to Jex et al and 3,045,036 to Jex et al. The aminofunctional silicones described in these references and their methods of preparation are hereby incorporated by reference.

In preparing the silicone polyether copolymers of this invention, the mole ratio of cyclic anhydride to hydroxyl groups linked to the polyether is not critical and may vary over a wide range. For example, the mole ratio of cyclic anhydride to hydroxy group may range from about 0.17 to 1 to 1:25 to 1 with the preferred ratio of cyclic anhydride to hydroxyl group being 0.33:1 to 1:1, with the proviso that at least one hydroxyl group per molecule is reacted with the cyclic anhydride.

In the subsequent reaction where the resultant carboxylic acid functional polyether is then reacted with the aminofunctional silicone fluid, the mole ratio of carboxlic acid radical to amine group linked to the silicone fluid may range from 0.17:1 to 1.25:1, with the proviso that at least one carboxylic acid radical per molecule be reacted with one amine group linked to the silicone fluid.

These silicone polyether copolymers have a variety of outstanding properties. For example, they can be prepared so that they are either soluble or insoluble in water. Also, they can be prepared so that they will crosslink when exposed to mositure to form rubbery films. Furthermore, they may be prepared to form stable water solutions which are curable upon the evaporation of water.

The silicone polyether copolymers of this invention may be used either alone or in combination with other materials which have been used to treat textile materials, such as tetrafluoroethylene emulsions, to impart certain properties to textile materials.

Surprisingly it has been found that when the silicone polyether copolymers of this invention have alkoxy groups linked to the silicone atoms, they may be added to, for example, a tetrafluoroethylene emulsion, to form a composition which cures to a rubbery, oleophobic and hydrophobic film.

Likewise, when textile materials are treated with a composition containing the curable silicone polyether copolymers and a tetrafluoroethylene emulsion, the resultant textile materials also exhibit a soft hand. However, when textile materials are treated solely with the tetrafluoroethylene emulsion, hard resinous discontinuous films are obtained and the treated textile material has a harsh hand.

The ratio of the curable silicone polyether copolymers of this invention to tetrafluoroethylene emulsion is not critical and may vary over a wide range. For example the amount of curable silicone polyether copolymers of this invention may vary from 1.0 percent to 99.0 percent by weight and the tetrafluorethylene emulsion may range from 99 percent to 1.0 percent by weight and more preferably the amount of curable silicone polyether copolymers of this invention may vary from 10 to 85 percent while the amount of tetrafluoroethylene emulsion may range 90 to 15 percent by weight based on the weight of the curable silicone polyether copolymers and tetrafluoroethylene emulsion. The amount of tetrafluoroethylene in the tetrafluoroethylene emulsions may range from about 20 to 50 percent by weight based on the total weight of the tetrafluororethylene emulsion.

Other materials which may be used in combination with the silicone polyether copolymers of this invention are lubricating agents, agents which impart abrasion resistance to the treated materials, materials which improve the fragrance of the treated materials, antistatic lubricants, fabric softeners, fire retardants, soil resistant materials and crease-proofing agents. Examples of crease-proofing agents which may be employed are aminoplast resins such as urea-formaldehyde resins, melamine-formaldehyde resins, and dimethylol dihydroxy ethylene urea, which may contain magnesium chloride and zinc nitrate as catalysts. Other crease-proofing resins are phenol-formaldehyde resins and hydroxyethyl methacrylate.

The silicone polyether copolymers of this invention may be applied in concentrated form or as an aqueous solution or in the form of dispersions in water or in organic solvents such as di-n-butylether, aromatic hydrocarbons, and/or chlorinated hydrocarbons.

When the silicon polyether copolymers are used as an aqueous solution or dispersion in the treatment of textile materials, the amount of silicone polyether copolymers dissolved or dispersed in water may vary over a wide range. Generally, the amount of silicone polyether copolymer present in an aqueous solution or dispersion may range from about 0.25 to 99 percent, preferably from about 1 to 60 percent and more preferably from about 2 to 50 percent by weight based on the weight of the silicone polyether copolymers and solvent.

The silicone polyether copolymers of this invention, and if desired other substances, may be applied to all textile materials, preferably organic textile materials on which organo-polysiloxanes have been or could have been applied heretofore. Examples of such textile materials are wool, cotton, rayon, hemp, natural silk, polypropylene, polyethylene, polyester, polyurethane, polyamide, cellulose acetate, polyacrylonitrile fibers, and mixtures of such fibers. The textile materials may consist of staple fibers or monofilaments.

The curable silicone polyether copolymers of this invention and other substances, if desired, may be applied to the textile materials by any means known in the art, such as by spraying, immersion, coating, calendering or by gliding the fibers across a base which has been saturated with the silicone polyether copolymers of this invention and other materials, if desired.

Generally, the solids add-on is in the range of from 0.025 to 20 percent and preferably from about 0.05 to 10 percent, based on the weight of the original textile material.

After the textile material has been treated, it is dried at an elevated temperature, e.g., from about 50° to 200° C. for a brief period of time, e.g., from about 3 to 15 minutes.

The treated textile material should contain from about 0.025 to about 10 percent by weight on a dry basis of the cured composition of this invention.

Textile materials treated with the silicone polyether copolymers of this invention possess all of the properties common to prior art textile materials, such as soft hand, with the additional property of being olephobic, hydrophobic and soil resistant.

Specific embodiments of this invention are further illustrated in the following examples in which all parts are by weight unless otherwise specified.

EXAMPLE 1

(a) Preparation of aminofunctional silicone fluid

A mixture containing 2960 parts of octamethylcyclotetrasiloxane, 599.4 parts of 2-aminoethyl-3-aminopropyltriethoxysilane and 1.7 parts of potassium hydroxide is heated to 145° C. and maintained at this temperature for three hours. The resultant product is cooled to 45° C., then 1.7 parts of acetic acid are added and the product filtered.

(b) Preparation of carboxylic acid functional polyether

A mixture containing 400 parts of an oxyethylene glycol having the formula

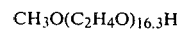

$$CH_3O(C_2H_4O)_{16.3}H$$

and 78.5 parts of phthalic anhydride is heated in a nitrogen atmosphere for 6 hours at 140° C. The product is cooled to 50° C. and filtered. A sample is analyzed and found to have an acid content of about 1.09 milliequivalents per gram. The theoretical value is calculated to be 1.1.

(c) Preparation of silicone polyether copolymer

About 89.8 parts of the carboxylic acid functional polyether (b) above and 66.6 parts of the aminofunctional silicon fluid (a) above are reacted at a temperature of about 45° C. to form an opaque yellow soft wax. A portion of the composition is dissolved in water and then placed in an oven at 168° C. After several minutes a rubbery film is obtained. The resultant product is analyzed by Nuclear Magnetic Resonance and Infrared. The analyses indicate that the resultant product has the formula

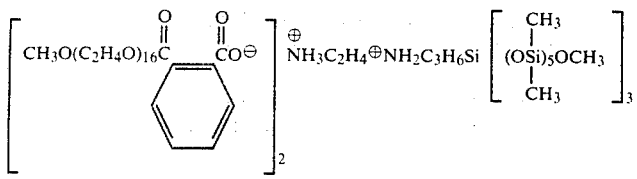

EXAMPLE 2

A mixture containing 400 parts of an oxyethylene glycol having the formula

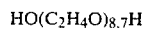

HO(C$_2$H$_4$O)$_{8.7}$H and 296.2 parts of phthalic anhydride is heated for 6.0 hours at 140° C. The resulting carboxylic acid functional polyether is cooled to room temperature. The acid content of the product is 2.33 milliequivalents per gram, whereas the theoretical value is 2.87.

About 133.2 parts of the reaction product are mixed with 69.6 parts of the aminofunctional silicone fluid of Example 1 (a) and agitated for one hour. The resultant product is analyzed by Nuclear Magnetic Resonance and Infrared. The analyses indicate that the product has the formula

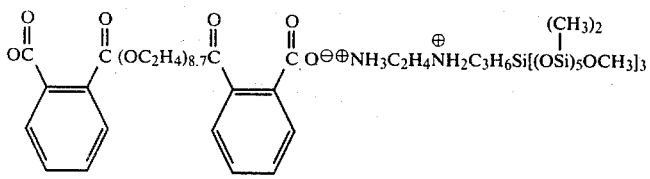

Aqueous solutions of this product from rubbery films upon evaporation of the water.

EXAMPLE 3

(a) Preparation of aminofunctional silicone fluid

A mixture containing 1445.5 parts of octamethylcyclotetrasiloxane, 1020 parts of eicosamethylnonasiloxane, 222 parts of 2-aminoethyl-3-aminopropyltrimethoxysilane, 222 parts of water and 2.6 parts of potassium hydroxide is heated to reflux and the methanol-water azeotrope is collected up to a temperature of 175° C. The resultant product is cooled to 90° C. then 2.6 parts of acetic acid are added and the resultant product filtered.

(b) Preparation of carboxylic acid functional polyether

A mixture containing about 1050 parts of an oxyethylene glycol having the formula

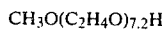

CH$_3$O(C$_2$H$_4$O)$_{7.2}$H and 300 parts of succinic anhydride are heated to 175° C. and then cooled to room temperature. Nuclear Magnetic Resonance analysis of the product shows the following groups to be present in the following mole ratio:

| Group | Found | Theoretical |
|---|---|---|
| $\overset{O}{\underset{\|}{C}}(CH_2)\overset{O}{\underset{\|}{C}}$ | 1.0 | 1.0 |
| $\overset{O}{\underset{\|}{C}}OH$ | 0.96 | 1.0 |
| CH$_3$O | 0.82 | 1.0 |
| C$_2$H$_4$O | 6.5 | 7.2 |
| $CH_2O\overset{O}{\underset{\|}{C}}O$ | 1.2 | 1.0 |

The resultant product is not soluble in hexamethyldisiloxane.

(c) Preparation of silicone polyether copolymer

About 270 parts of the carboxylic acid functional polyether (b) prepared above is mixed with 677.7 parts of the aminofunctional silicone fluid (a) prepared above to form a yellow translucent liquid having a viscosity of 2,710 cs. at 25° C. The product is insoluble in water, but forms a clear solution when mixed with hexamethyldisiloxane. Subsequent Nuclear Magnetic Resonance and Infrared analyses indicate a product having the formula

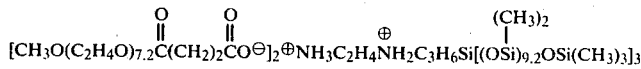

This example shows that the carboxylic acid functional polyether prepared in (b) above is insoluble in hexamethyldisiloxane, whereas the silicon polyether copolymer preprared in (c) above is soluble in hexamethyldisiloxane.

EXAMPLE 4

A mixture containing 1110 parts of an oxyethylene glycol of the formula

CH$_3$O (C$_2$H$_4$O)$_{14}$H and 220.2 parts of succinic anhydride is heated to 175° C. Nuclear Magnetic Resonance analysis of the product shows that the following groups are present in the indicated mole ratio

| Group | Found | Theoretical |
| --- | --- | --- |
| $C_2H_4O$ | 10.4 | 11.8 |
| $HOC(=O)$ | 1.0 | 1.0 |
| $C(=O)(CH_2)_2C(=O)$ | 1.98 | 2.0 |

About 260 parts of the above carboxylic acid functional polyether are mixed with 451.8 parts of the aminofunctional silicone fluid of Example 3 (a) and agitated for 30 minutes during which time an exotherm is observed. The resultant product is a white colored liquid which is insoluble in hexamethyldisiloxane, but is easily dispersed in water to form an emulsion. Subsequent Nuclear Magnetic analysis indicates a product having the formula

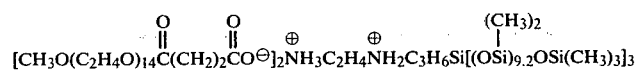

EXAMPLE 5

(a) Preparation of aminofunctional silicone fluid

An aminofunctional silicone fluid is prepared by reacting 651.2 parts of octamethylcyclotetrasiloxane with 2040 parts of eicosamethylnonasiloxane, 444 parts of 3-aminopropyltriethoxysilane, 444 parts of water and 2.6 parts of potassium hydroxide. The mixture is heated to reflux and the ethanol-water azeotrope is collected up to 175° C. The resultant product is cooled to 90° C. and 2.6 parts of acetic acid are added. The product is then filtered.

(b) Preparation of silicone polyether copolymer

About 90 parts of the carboxylic acid functional polyether prepared in accordance with the procedure described in Example 3 (b) are mixed with 287.4 parts of the aminofunctional silicone fluid (a) above and agaitated for one hour during which time the temperature increased to 50° C. A clear liquid is obtained which has a viscosity of 879 cs. at 25° C. and is soluble in water. Nuclear Magnetic Resonance analysis of the product shows that the following groups are present in the indicated mole ratio.

| Group | Found | Calculated |
| --- | --- | --- |
| $CH_2OC(=O)$ | 1.19 | 1.0 |
| $C_2H_4O$ | 7.0 | 7.2 |
| $Si(CH_3)_2$ | 19.1 | 19.5 |

The product is represented by the formula

EXAMPLE 6

The product obtained from Example 5 is mixed with 20 parts of heptane. The mixture is heated to reflux and water is formed which azetropes with the heptane and phase separates upon condensation. The volatiles are removed in vacuum up to a temperature of about 190° C. A yellow liquid having a viscosity of 300 cs. at 25° C. is obtained. The product is readily dispersed in water to form an emulsion and is represented by the formula

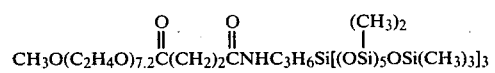

EXAMPLE 7

About 450 parts of the carboxylic acid functional polyether prepared in accordance with Example 3 (b) are mixed with 666 parts of the aminofunctional silicone fluid prepared in accordance with the procedure described in Example 1(a).

A straw colored liquid having a viscosity of 1187 cs. at 25° C. is obtained. The product is water soluble and an aqueous solution of the product formed a rubbery film upon evaporation of the water. The aqueous solutions are stable for up to 6 months. Analysis of the product by Nuclear Magnetic Resonance and Infrared shows a product having the formula

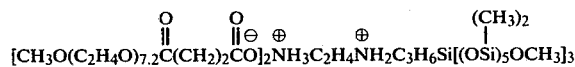

EXAMPLE 8

(a) Preparation of aminofunctional silicon fluid

About 1050 parts of octamethylcyclotetrasiloxane are mixed with 1771 parts of eicosamethylnonasiloxane, 386 parts of 2-aminoethyl-3-aminopropyltrimethoxysilane, 386 parts of distilled water and 5.2 parts of potassium hydroxide. The mixture is heated to reflux and the methanol-water azeotrope is collected up to a temperature of 175° C. The mixture is cooled to 90° C., then 5.2 parts of acetic acid are added and then filtered.

(b) Preparation of carboxylic acid functional polyether

About 317.4 parts of an oxyethylene-oxypropylene glycol copolymer having a molecular weight of approximately 800 and a mole ratio of oxyethylene to oxypropylene units of 1 to 1 are mixed with 20 parts of succinic anhydride. The mixture is heated to 175° C. and then cooled to room temperature. A sample is analyzed by Infrared and found to contain less than one percent by weight of unreacted succinic anhydride.

(c) Preparation of silicone polyether copolymers

A mixture containing 69.7 parts of carboxylic acid functional polyether (b) above and 26.7 parts of the amino-functional silicone fluid (a) above is mixed for 0.5 hour. The resultant product is a yellow opaque grease. It is readily dispersed in water forming a translucent dispersion. The dispersion does not separate even when centrifuged. Nuclear Magnetic Resonance and Infrared analyses show that the product has the formula

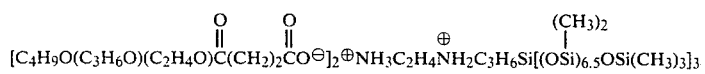

$[C_4H_9O(C_3H_6O)(C_2H_4O)\overset{O}{\overset{\|}{C}}(CH_2)_2\overset{O}{\overset{\|}{C}}O^{\ominus}]_2\overset{\oplus}{N}H_3C_2H_4NH_2C_3H_6Si[(OSi)_{6.5}OSi(CH_3)_3]_3\overset{(CH_3)_2}{|}$

EXAMPLE 9

About 333 parts of the silicone polyether copolymer preprared in accordance with the procedure of Example 7 are dissolved in 667 parts of water. About 100 parts of the solution are then mixed with 1244 parts of water and 50 parts of a teflon emulsion containing about 25 percent by weight of teflon based on the weight of the emulsion (available from E. I. DuPont as TEFLOR MF). A stable emulsion is obtained which upon drying forms a continuous rubbery film.

COMPARISON EXAMPLE V₁

About 2 parts of the teflon emulsion described in Example 9 are placed in an aluminum dish and evaporated in a heated oven to dryness. A solid resinous discontinuous film is obtained.

EXAMPLE 10

The emulsion prepared in Example 9 is used to treat Dacron 54 and Spun Nylon 200 fabric (available from Test Fabrics). A 7"×7" piece of each fabric is dipped in the emulsion for 30 seconds. The coated fabrics are then dried for 15 minutes at 90° C. The water repellency properties of the treated fabrics are determined in accordance with AATCC Test Method 22-1971, "Water Repellency Spray Test". The oil repellency properties of the treated fabrics are determined in accordance with AATCC Test Method 118'-1978 "Oil Repellency: Hydrocarbon Resistance Test". The following table shows the results of the tests.

| Treating Agent | Oil Repellency | | Water Repellency | |
|---|---|---|---|---|
| | Dacron | Spun Nylon 200 | Dacron | Spun Nylon 200 |
| None | 0 | 0 | 70 | 0 |
| Example 7 | 0 | 0 | 0 | 0 |
| Example 9 | 3 | 1 | 70 | 50 |
| Comparison Example V₁ | 4 | 3 | 50 | 0 |

What is claimed is:

1. Silicone polyether copolymers of the general formula

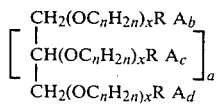

where R is a radical selected from the group consisting of

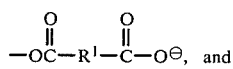

in which the radical R is linked to the polyether through an ester linkage, $R^1$ is a divalent hydrocarbon radical selected from the group consisting of $(-CH_2)_y$, $-CH=CH-$ and a cyclic radical selected from the group consisting of $C_6H_4$, $C_6H_8$ and $C_{10}H_6$; A is a silicone containing monovalent or divalent radical selected from the group consisting of

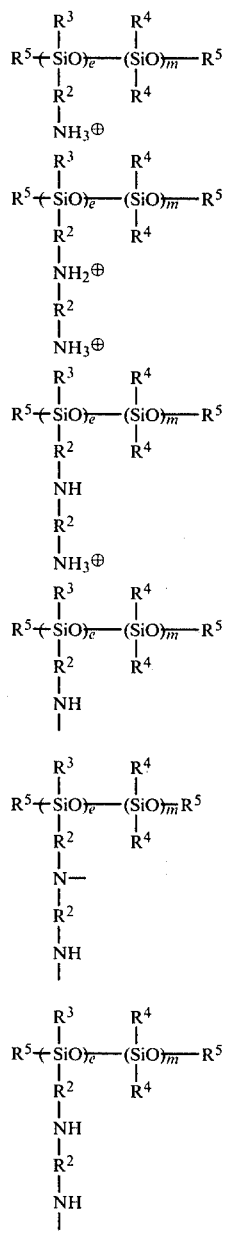

$R^2$ is selected from the group consisting of saturated divalent hydrocarbon radicals, hydrocarbonoxy radicals in which the hydrocarbon group is linked to the silicon by a carbon bond and the oxygen is in the form of an ether linkage, and unsaturated divalent hydrocarbon radicals, $R^3$ is selected from the group consisting of monovalent hydrocarbon radicals having from 1 to 18 carbon atoms, alkoxy radicals having from 1 to 18 carbon atoms and $OSi(R^4)_3$ radicals, $R^4$ is a monovalent hydrocarbon radical having from 1 to 18 carbon atoms, $R^5$ is a monovalent radical selected from the group consisting of $O_{0.5}Si(R^4)_3$ and $O_{0.5}R^4$, where $R^4$ is the same as above, and when R is cationic, then A must be anionic and when R is nonionic then A must be nonionic, a is a number of from 0 to 4, b, c and d are each numbers of from 0 to 1, the sum of b, c and d must be at least 1 when A is a monovalent radical and when A is a divalent radical b, c and d must be at least 0.5 and up to 3, with the proviso that when c is greater than 0, then a must be at least 1, e is a number of from 1 to 200, m is a number of from 1 to 20,000, n is 2, 3 or 4, x is a number of from 1 and up to 400, and y is a number of from 0 to 8.

2. The silicone polyether copolymers of claim 1, wherein A is a radical of the formula

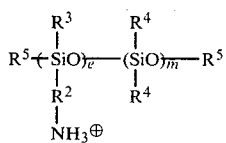

$R^2$ is selected from the group consisting of saturated divalent hydrocarbon radicals, hydrocarbonoxy radicals in which the hydrocarbon group is linked to the silicon by a carbon bond and the oxygen is in the form of an ether linkage, and unsaturated divalent hydrocarbon radicals, $R^3$ is selected from the group consisting of monovalent hydrocarbon radicals having from 1 to 18 carbon atoms, alkoxy radicals having from 1 to 18 carbon atoms and $OSi(R^4)_3$ radicals, $R^4$ is a monovalent hydrocarbon radical having from 1 to 18 carbon atoms, $R^5$ is a monovalent radical selected from the group consisting of $O_{0.5}Si(R^4)$ and $O_{0.5}R^4$, where $R^4$ is the same as above, e is a number of from 1 to 200 and m is a number of from 1 to 20,000.

3. The silicone polyether copolymers of claim 1, wherein A is a radical of the formula

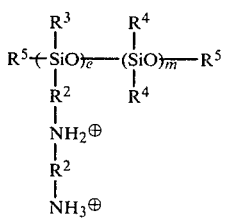

$R^2$ is selected from the group consisting of saturated divalent hydrocarbon radicals, hydrocarbonoxy radicals in which the hydrocarbon group is linked to the silicon by a carbon bond and the oxygen is in the form of an ether linkage, and unsaturated divalent hydrocarbon radicals, $R^3$ is selected from the group consisting of monovalent hydrocarbon radicals having from 1 to 18 carbon atoms, alkoxy radicals having from 1 to 18 carbon atoms and $OSi(R^4)_3$ radicals, $R^4$ is a monovalent hydrocarbon radical having from 1 to 18 carbon atoms, $R^5$ is a monovalent radical selected from the group consisting of $O_{0.5}Si(R^4)_3$ and $O_{0.5}R^4$, where $R^4$ is the same as above, e is a number of from 1 to 200 and m is a number of from 1 to 20,000.

4. The silicone polyether copolymers of claim 1, wherein A is a radical of the formula

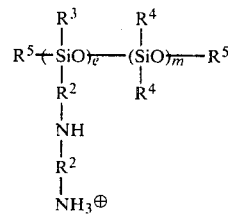

$R^2$ is selected from the group consisting of saturated divalent hydrocarbon radicals, hydrocarbonoxy radicals in which the hydrocarbon group is linked to the silicon by a carbon bond and the oxygen is in the form of an ether linkage, and unsaturated divalent hydrocarbon radicals, $R^3$ is selected from the group consisting of monovalent hydrocarbon radicals having from 1 to 18 carbon atoms, alkoxy radicals having from 1 to 18 carbon atoms and $OSi(R^4)_3$ radicals, $R^4$ is a monovalent hydrocarbon radical having from 1 to 18 carbon atoms, $R^5$ is a monovalent radical selected from the group consisting of $O_{0.5}Si(R^4)_3$ and $O_{0.5}R^4$, where $R^4$ is the same as above, e is a number of from 1 to 200 and m is a number of from 1 to 20,000.

5. The silicone polyether copolymers of claim 1, wherein A is a radical of the formula

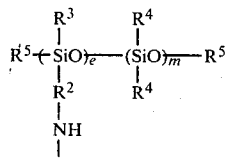

$R^2$ is selected from the group consisting of saturated divalent hydrocarbon radicals, hydrocarbonoxy radicals in which the hydrocarbon group is linked to the silicon by a carbon bond and the oxygen is in the form of an ether linkage, and unsaturated divalent hydrocarbon radicals, $R^3$ is selected from the group consisting of monovalent hydrocarbon radicals having from 1 to 18 carbon atoms, alkoxy radicals having from 1 to 18 carbon atoms and $OSi(R^4)_3$ radicals, $R^4$ is a monovalent hydrocarbon radical having from 1 to 18 carbon atoms, $R^5$ is a monovalent radical selected from the group consisting of $O_{0.5}Si(R^4)_3$ and $O_{0.5}R^4$, where $R^4$ is the same as above, e is a number of from 1 to 200 and m is a number of from 1 to 20,000.

6. The silicone polyether copolymers of claim 1, wherein A is a radical of the formula

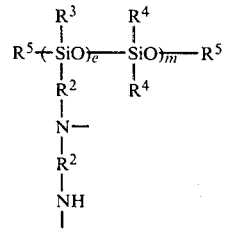

$R^2$ is selected from the group consisting of saturated divalent hydrocarbon radicals, hydrocarbonoxy radicals in which the hydrocarbon group is linked to the silicon by a carbon bond and the oxygen is in the form of an ether linkage, and unsaturated divalent hydrocarbon radicals, $R^3$ is selected from the group consisting of monovalent hydrocarbon radicals having from 1 to 18 carbon atoms, alkoxy radicals having from 1 to 18 carbon atoms and $OSi(R^4)_3$ radicals, $R^4$ is a monovalent hydrocarbon radical having from 1 to 18 carbon atoms, $R^5$ is a monovalent radical selected from the group consisting of $O_{0.5}Si(R^4)_3$ and $O_{0.5}R^4$, where $R^4$ is the same as above, e is a number of from 1 to 200 and m is a number of from 1 to 20,000.

7. The silicone polyether copolymers of claim 1, wherein R is a radical of the formula

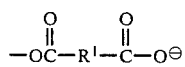

$R^1$ is a divalent hydrocarbon radical selected from the group consisting of $(-CH_2)_y$, $-CH=CH-$ and an aryl radical selected from the group consisting of $C_6H_4$, $C_6H_8$ and $C_{10}H_6$.

8. The silicone polyether copolymers of claim 1, wherein R is a radical of the formula

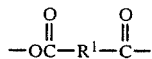

$R^1$ is a divalent hydrocarbon radical selected from the group consisting of $(-CH_2)_y$, $-CH=CH-$ and an aryl radical selected from the group consisting of $C_6H_4$, $C_6H_8$ and $C_{10}H_6$.

9. The silicone polyether copolymers of claim 1, wherein $R^1$ is a divalent hydrocarbon radical of the formula

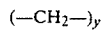

where y is a number of from 0 to 8.

10. The silicone polyether copolymers of claim 1, wherein $R^1$ is a radical of the formula $C_6H_8$.

11. A silicone polyether copolymer of the formula

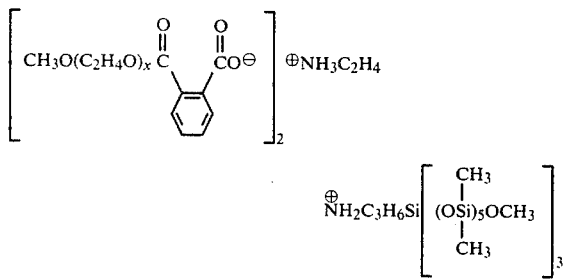

where m is a number of from 1 to 20,000 and x is a number of from 1 to 400.

12. A silicone polyether copolymer of the formula

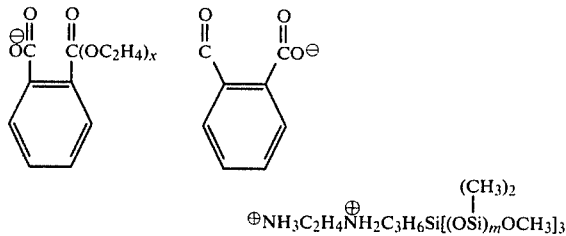

where m is a number of from 1 to 20,000 and x is a number of from 1 to 400.

13. A silicone polyether copolymer of the formula

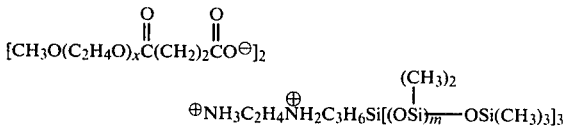

where m is a number of from 1 to 20,000 and x is a number of from 1 to 400.

14. A silicone polyether copolymer of the formula

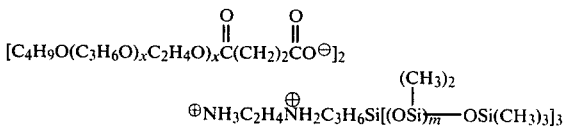

where m is a number of from 1 to 20,000 and x is a number of from 1 to 400.

15. A process for preparing the silicone polyether copolymers of claim 1 which comprises reacting an oxyalkylene glycol with a cyclic anhydride in a mol ratio of cyclic anhydride to hydroxyl group of 0.33:1 to 1:1 at a temperature of from 80° to 185° C. to form a half ester and thereafter reacting the resultant product with an aminofunctional siloxane at a temperature of from 25° to 110° C.

16. The process of claim 15, wherein the silicone polyether copolymers are heated to a temperature above 115° C. to form the corresponding amides.

17. The process of claim 15, wherein the oxyalkylene glycols are represented by the formula

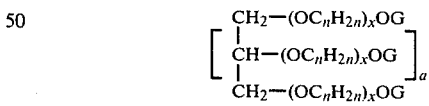

where G is selected from the group consisting of hydrogen or an alkyl radical having from 1 to 18 carbon atoms, in which at least one G must be hydrogen, a is a number of from 0 to 4, n is 2, 3 or 4, and x is a number of at least 1 and up to 400.

* * * * *